Nov. 1, 1955 F. W. ANDERSON Plant Pat. 1,429
NECTARINE TREE
Filed Feb. 4, 1955
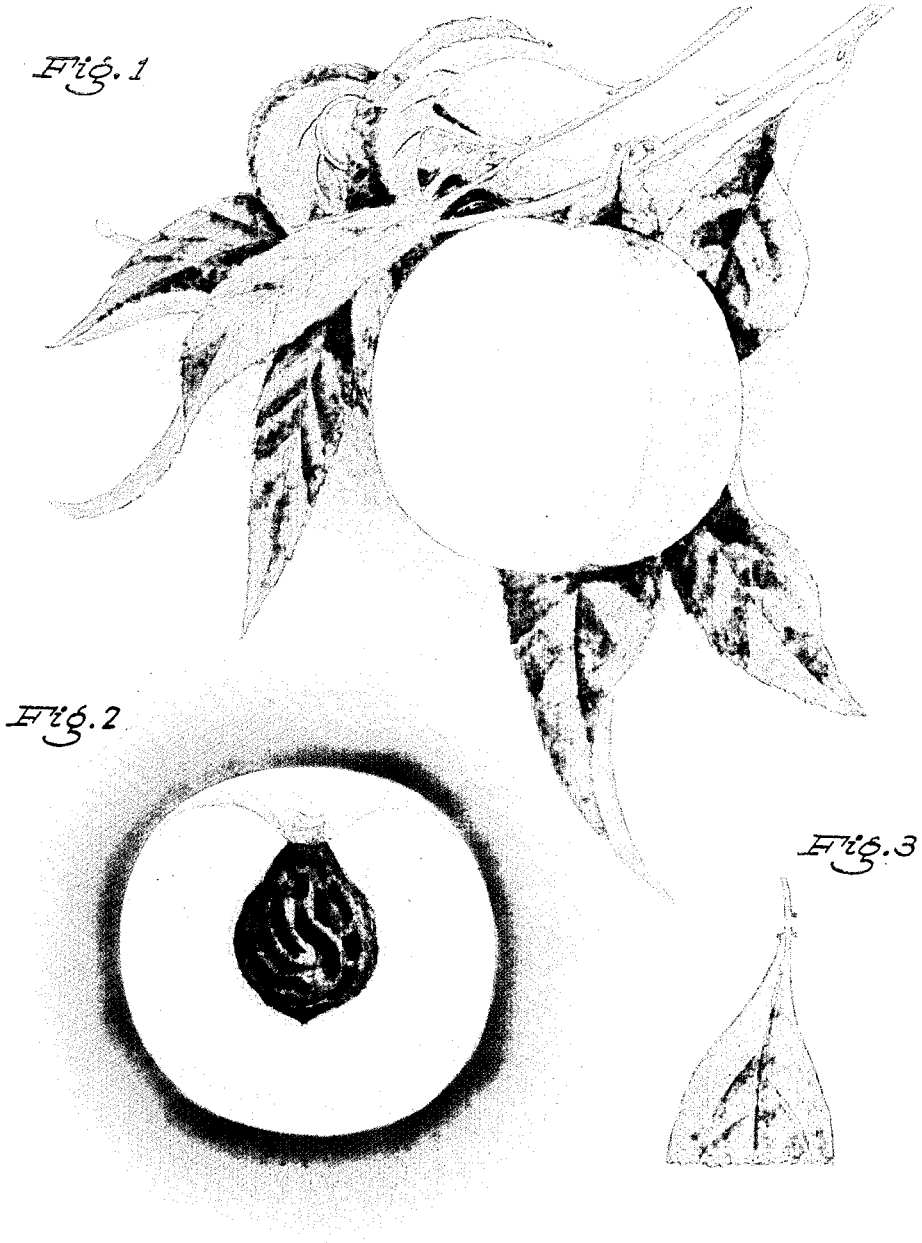
WITNESS
Addison E. Avery
INVENTOR
Frederic W. Anderson
Webster & Webster
ATTYS.

United States Patent Office

Plant Pat. 1,429
Patented Nov. 1, 1955

1,429

NECTARINE TREE

Frederic W. Anderson, Merced, Calif.

Application February 4, 1955, Serial No. 486,303

1 Claim. (Cl. 47—62)

This invention relates to a new and distinct variety of nectarine tree which bears yellow fleshed freestone fruit having yellow skin overspread with red to a substantial extent; the variety being an F–2 cross of the Le Grand nectarine (United States Plant Patent 549) and the Halehaven peach (unpatented).

The instant variety was originated by me in my experimental nursery and orchard located at Le Grand, Merced County, California, during the course of a continuing plant breeding program seeking commercially desirable varieties of fruit, particularly nectarines.

The original plant was grown under conditions of careful observation, and when it grew to maturity I recognized that the fruit had certain distinct characteristics which made it quite desirable for commercial use. I therefore selected the variety for reproduction; asexual reproduction having been accomplished by top working—specifically budding—on mature orchard trees in my experimental orchard located as above. These asexual reproductions were found to run true in all respects.

In comparison to other commercial varieties of nectarines the fruit here is somewhat similar in size, shape, and color to that of the Sun Grand nectarine (United States Plant Patent 974), but ripens approximately one week later, and does not remain firm for as long a period of time.

In comparison to the Freedom nectarine (United States Plant Patent 1,161) the fruit of my present variety ripens approximately one week earlier, is somewhat smaller in size, and somewhat less firm in flesh, but has more red exterior color.

In the drawings:

Fig. 1 is an elevation showing one of the fruit, together with a twig and leaves.

Fig. 2 is a sectional elevation of one of the fruit with the stone exposed.

Fig. 3 is a fragmentary elevation of a leaf.

Referring now more specifically to the pomological details of this new and distinct variety of nectarine tree, the following is an outline description thereof; all major color plate identifications being by reference to Maerz and Paul Dictionary of Color:

Tree:
- *Size.*—Large.
- *Vigor.*—Vigorous.
- *Growth.*—Upright to spreading.
- *Density.*—Dense.
- *Hardiness.*—Hardy.
- *Production.*—Very productive.
- *Bearing.*—Regular bearer.

Trunk:
- *Size.*—Medium.
- *Surface.*—Medium.

Branches:
- *Size.*—Medium.
- *Surface.*—Medium.

- *Color.*—Old branches—brownish grey; new branches—green.
- *Lenticels.*—Number—medium; size—large.

Leaves:
- *Size.*—Medium. Average length—5½" to 6"; width—1⅛" to 1⅝".
- *Form.*—Lanceolate; acutely pointed; medium thickness.
- *Color.*—Top side—medium green (22–L–5). Under side—lighter green (21–J–6).
- *Surface.*—Smooth.
- *Margin.*—Crenate.
- *Petiole.*—Medium length; medium thickness.
- *Glands.*—Average number—two to three. Opposite to alternate. Medium size. Form—globose. Color—yellowish green. Position—base of blade and petiole.
- *Stipules.*—Two; small.

Flower buds:
- *Size.*—Medium.
- *Length.*—Medium.
- *Form.*—Obtuse.

Flowers:
- *Date of bloom.*—March 10, 1954; about with Le Grand nectarine. Medium blooming period compared with other varieties.
- *Size.*—Large.
- *Color.*—Pink.

Fruit:
- *Maturity when described.*—Eating ripe.
- *Date of first picking.*—July 20, 1954.
- *Date of last picking.*—July 30, 1954.
- *Size.*—Medium. Average diameter axially—2¼" to 3". Average transverse in suture plane—2" to 2¾".
- *Form.*—Axial plane—symmetrical, with tendency to be slightly conical, flattened at apex. Suture plane—unsymmetrical, with tendency to be oblate, but compressed slightly on the side of the ventral suture near the apex.
- *Suture.*—Ventral suture distinct. Shallow, slightly deeper toward apex. Extends from base to slightly beyond apex.
- *Ventral surface.*—Rounded slightly, compressed towards apex. Lips equal.
- *Cavity.*—Elongated in suture plane, with suture showing on both sides. Average depth—¼" to ⅝"; average breadth—¾" to 1⅛".
- *Base.*—Rounded.
- *Apex.*—Slightly depressed.
- *Pistil point.*—Slightly oblique.

Skin:
- *Texture.*—Medium thickness; medium tender; tenacious to flesh.
- *Tendency to crack.*—None in dry season.
- *Down.*—Wanting.
- *Color.*—Yellow (9–K–6, shading to 9–L–8, shading to 11–L–12), overspread to a substantial extent with red (4–K–12, shading to 4–L–9).

Flesh:
- *Amygdalin.*—Wanting.
- *Juice.*—Moderate.
- *Texture.*—Firm; crisp; melting.
- *Fibers.*—Few.
- *Ripens.*—Even.
- *Flavor.*—Rich; some acid.
- *Aroma.*—Distinct.
- *Eating quality.*—Good.
- *Color.*—Yellow (9–K–6 shading to 9–L–7), with red mottling (5–L–7) next to stone throughout.

Stone:

*Type.*—Free. Parts from flesh smoothly.

*Size.*—Medium. Average length—1½″; average breadth—1¼″; average thickness—1″.

*Form.*—Ovoid.

*Base.*—Straight.

*Hilum.*—Narrow.

*Apex.*—Rounded.

*Sides.*—Equal.

*Surface.*—Irregularly furrowed throughout; ridged near base; pitted toward base.

*Ridges.*—Rounded; interrupted.

*Pits.*—Circular.

*Dorsal edge.*—Full, with shallow broad grooves.

*Tendency to split.*—Slight.

*Color.*—Brown (8–L–1), with pits shaded darker brown (8–A-6).

Use: Market; local.

Keeping quality: Good.

Shipping quality: Medium.

The tree and its fruit herein described may vary in slight detail due to climatic and soil conditions under which the variety may be grown.

The following is claimed:

A new and distinct variety of nectarine tree, as illustrated and described, which bears yellow fleshed, freestone fruit having yellow skin overspread with red to a substantial extent, characterized—in comparison to the Sun Grand nectarine—by fruit generally similar in size, shape, and color but ripening approximately one week later and not remaining firm for as long a period of time; and characterized—in comparison with the Freedom nectarine—by fruit ripening approximately one week earlier, slightly smaller in size, and less firm in flesh, but having more red exterior color.

No references cited.